United States Patent [19]

Schoch et al.

[11] 4,321,412
[45] Mar. 23, 1982

[54] PREPARATION OF AROMATIC ALDEHYDES BY THE SOMMELET REACTION

[75] Inventors: Werner Schoch, Eschelbronn; Michael Kroener, Mannheim; Rudi Widder, Leimen, all of Fed. Rep. of Germany

[73] Assignee: BASF Aktiengesellschaft, Ludwigshafen, Fed. Rep. of Germany

[21] Appl. No.: 197,159

[22] Filed: Oct. 15, 1980

[30] Foreign Application Priority Data

Oct. 24, 1979 [DE] Fed. Rep. of Germany ....... 2942894

[51] Int. Cl.³ .................... C07C 45/00; C07C 45/42; C07C 45/43
[52] U.S. Cl. .................................................. 568/436
[58] Field of Search ................................ 568/436, 639

[56] References Cited

U.S. PATENT DOCUMENTS 4,085,147  4/1978  Rosinger et al. ............... 568/639 X
4,108,904  8/1978  Brown et al. ................... 568/639 X

FOREIGN PATENT DOCUMENTS 5533 of 1914 United Kingdom ................ 568/436

OTHER PUBLICATIONS

Adams et al., Organic Reactions, vol. VIII, (1954), 197–217.

*Primary Examiner*—Bernard Heflin
*Attorney, Agent, or Firm*—Oblon, Fisher, Spivak, McClelland & Maier

[57] ABSTRACT

In a process for the preparation of aromatic monoaldehydes by reacting monochlorinated methylaromatics with hexamethylenetetramine by a Sommelet reaction, the improvement that in place of pure chloromethylaromatics the chlorination mixtures produced by photochlorination of the methylaromatics are employed and are treated with hexamethylenetetramine without prior working up, after which the Sommelet reaction is allowed to take place.

2 Claims, No Drawings

PREPARATION OF AROMATIC ALDEHYDES BY THE SOMMELET REACTION

BACKGROUND OF THE INVENTION

1. Field of the Invention

This invention relates to a method of producing aromatic aldehydes and more particularly to an improved method of carrying out the Sommelet reaction.

2. Description of the Prior Art

The reaction of monohalomethylaromatics with urotropin (hexamethylenetetramine), giving aromatic aldehydes, is an old-established reaction referred to as the Sommelet reaction.

In this, monohalomethylaromatics are reacted with urotropin (hexamethylenetetramine), giving the corresponding arylalkylurotropinium halide as an intermediate which undergoes rearrangement to the salt of a Schiff base; at the same time, methyleneimine is formed by reaction of formaldehyde and ammonia, the ammonia resulting from the decomposition of the urotropin. Ultimately, the aldehyde and methylamine are formed from these two molecules by hydride shift. A comprehensive review has been given by S. J. Angyal, Org. Reactions 8 (1954), 197 et seq. It emerges from this article and also from disclosures elsewhere that pure monohalomethylaromatics, for example benzyl chloride, p-xylyl chloride and the like, are required as starting materials if the reaction is to be carried out as a one-vessel reaction.

In general, the reaction has hitherto been carried out in solvents, such as alcohol, aqueous alcohol or glacial acetic acid.

Where an unpurified starting material was used, earlier authors have recommended that the intermediate, namely the arylalkylurotropinium halide, should be isolated and only then used to carry out the Sommelet reaction.

Using these methods, the maximum yield achieved is, according to Angyal, loc. cit., about 70% of theory.

SUMMARY OF THE INVENTION

Since aromatic aldehydes are important intermediates and since, in particular, there are no very satisfactory alternative methods for the economical preparation of benzaldehyde homologs, optimization of the Sommelet reaction is an object of the present invention, the starting materials being readily available.

We have found that this object is achieved and that yields of aromatic aldehydes of more than 80% of theory, based on monochloromethylaromatics, are obtained if a crude mixture obtained by photochlorination of methylaromatics is subjected, without further working up and purification, to a Sommelet reaction in an aqueous medium. Accordingly, in the improved process, a crude chlorination mixture obtained by photochlorination of methylaromatics with less than the stoichiometric amount of chlorine required for the monochlorination products is employed in place of pure monochlorinated methylaromatics, this mixture is treated, without prior working up, with hexamethylenetetramine, and the Sommelet reaction is then carried out with addition of water.

DESCRIPTION OF THE PREFERRED EMBODIMENTS

The surprising aspect of this improved process is that in spite of the high proportion of by-products, pure products are ultimately obtained without significant difficulties in working up. A particularly noteworthy aspect in that the more highly chlorinated methylaromatics present in the starting material do not interfere with the reaction.

The starting mixtures are obtained by photochlorination of methylaromatics. For the purposes of the present invention, methylaromatics are especially mononuclear or binuclear aromatics containing 1, 2 or 3 methyl groups. Specific examples are toluene, p-tert.-butyltoluene, p-xylene and α- and β-methylnaphthalene. Mixtures may also be employed, and these produce the corresponding aldehyde mixtures.

The photochlorination of the methylaromatics is carried out by employing the chlorine in less than the stoichiometric amount for the monochlorination of the methyl group, so as substantially to suppress polychlorination, i.e. substantially to avoid the formation of, for example, benzal chloride or dichlorinated p-xylene. As a result of using less than the stoichiometric amount of chlorine, the chlorination mixture obtained still contains up to 50% by weight of unconverted methylaromatics. Furthermore, an unavoidable proportion (2–4% by weight) of nuclear-substituted aromatics, and 4–6% by weight of products with polychlorinated side chains, are present.

The reaction is carried out by combining the chlorinated mixture with urotropin in the molar ratio of from 1:1 to 1:1.5, based on pure monochloromethylaromatics, and mechanically agitating the batch for from about 5 to 30 minutes, for example with a stirrer, in the absence of oxygen, advantageously under a nitrogen atmosphere.

Water, in a weight ratio to pure chloromethylaromatics of from about 1:2 to 3:1, is then added, and the mixture is refluxed for from about 1½ to 5 hours.

A mineral acid, e.g. concentrated hydrochloric acid, is then added in an amount sufficient to give a pH of about 3–4 in the aqueous phase, the mixture is heated for about 15 minutes at up to 100° C. and is allowed to cool, and the aqueous phase is separated off.

The organic phase is then fractionated, with or without the addition of a small amount of a stabilizer, such as hydroquinone. The aldehyde obtained is separated off, unconverted methylaromatics are recycled to the chlorination, and the by-products are either discarded or used for other purposes.

The aldehydes are obtained in yields of over 80% of theory, based on chloromethylaromatics, and in more than 99% purity.

The process is particularly important for the preparation of p-tolylaldehyde from p-xylyl chloride or the preparation of benzaldehyde from benzyl chloride.

The representative Example which follows illustrates the invention.

EXAMPLE 1,050.1 g of chlorinated p-xylene, consisting of 47.61% of p-xylyl chloride, 43.76% of p-xylene, 3.6% of nuclear-chlorinated p-xylene and 5.03% of polychlorinated p-xylenes, the mixture containing exactly 500 g (3.55 moles) of p-xylyl chloride, are stirred with 546.7 g (3.9 moles) of urotropin for 15 minutes, under nitrogen, in a 4 liter three-necked flask equipped with a reflux condenser and stirrer.

1,000 g of water are then added and the mixture is refluxed for 3 hours. It is then allowed to cool, brought to a pH of 3–4 at room temperature with 170 ml of concentrated HCl, and then refluxed for a further 15 minutes.

Thereafter, the mixture is allowed to cool again and the aqueous phase is separated off. The organic phase is distilled after addition of 0.01 g of hydroquinone.

152.74 g (82.22% of theory) of 99% pure p-tolylaldehyde are obtained.

We claim:

1. In a process for the preparation of aromatic monoaldehydes by reacting methylaromatics, which are monochlorinated in a methyl group, with hexamethylenetetramine by a Sommelet reaction, subjecting the reaction mixture to acid hydrolysis and separating off the monoaldehydes formed, the improvement that in place of pure monochlorinated methylaromatics a crude chlorination mixture which has been produced by photochlorination of methylaromatics with less than the stoichiometric amount of chlorine required for the formation of monochlorination products is employed, this mixture is treated with hexamethylenetetramine, and the Sommelet reaction is then carried out with addition of water, with the proviso that the steps of treating the mixture with hexamethylenetetramine and carrying out the Sommelet reaction take place in a single vessel without isolation of an intermediate product.

2. A process as claimed in claim 1, wherein the crude mixture obtained by photochlorinating p-xylene or toluene is employed.

* * * * *